(12) United States Patent
Kang et al.

(10) Patent No.: US 9,492,133 B2
(45) Date of Patent: Nov. 15, 2016

(54) APPARATUS AND METHOD FOR ACQUIRING OPTIMAL MULTI-ENERGY X-RAY IMAGE

(71) Applicant: SAMSUNG ELECTRONICS CO., LTD., Suwon-si (KR)

(72) Inventors: Dong Goo Kang, Suwon-si (KR); Sung Hoon Kang, Suwon-si (KR); Sung Su Kim, Yongin-si (KR); Young Hun Sung, Hwaseong-si (KR); Hyun Hwa Oh, Hwaseong-si (KR); Seok Min Han, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 340 days.

(21) Appl. No.: 13/845,742

(22) Filed: Mar. 18, 2013

(65) Prior Publication Data

US 2014/0119506 A1    May 1, 2014

(30) Foreign Application Priority Data

Oct. 25, 2012  (KR) .................. 10-2012-0118755

(51) Int. Cl.
*A61B 6/00* (2006.01)
*A61B 6/04* (2006.01)

(52) U.S. Cl.
CPC ............ *A61B 6/502* (2013.01); *A61B 6/405* (2013.01); *A61B 6/481* (2013.01); *A61B 6/482* (2013.01); *A61B 6/545* (2013.01); *A61B 6/583* (2013.01); *A61B 6/0414* (2013.01); *A61B 6/486* (2013.01); *A61B 6/5258* (2013.01); *A61B 6/544* (2013.01)

(58) Field of Classification Search
CPC .... A61B 6/0414; A61B 6/405; A61B 6/481; A61B 6/482; A61B 6/486; A61B 6/502; A61B 6/5258; A61B 6/544; A61B 6/545; A61B 6/583
See application file for complete search history.

(56) References Cited

U.S. PATENT DOCUMENTS

| | | | |
|---|---|---|---|
| 5,148,460 A * | 9/1992 | Aichinger | 378/37 |
| 2003/0095624 A1* | 5/2003 | Eberhard et al. | 378/37 |
| 2005/0069086 A1* | 3/2005 | Deych et al. | 378/112 |
| 2006/0058624 A1 | 3/2006 | Kimura | |
| 2007/0140408 A1 | 6/2007 | Takiura et al. | |
| 2007/0140428 A1 | 6/2007 | Toth | |
| 2013/0272495 A1* | 10/2013 | Bullard et al. | 378/37 |

FOREIGN PATENT DOCUMENTS

| | | |
|---|---|---|
| JP | 2006-94956 A | 4/2006 |
| JP | 2009-125250 A | 6/2009 |
| JP | 2009-261519 A | 11/2009 |
| JP | 2010-234003 A | 10/2010 |
| JP | 2011-92412 A | 5/2011 |
| KR | 10-2005-0024616 A | 3/2005 |

* cited by examiner

*Primary Examiner* — Glen Kao
(74) *Attorney, Agent, or Firm* — Sughrue Mion, PLLC

(57) ABSTRACT

An apparatus and method for acquiring an optimal MEX image may include an X-ray source to generate an X-ray and to irradiate the X-ray, an energy identification detector to acquire a MEX image that is generated when the irradiated X-ray penetrates an object, and an optimal MEX processor to generate an optimal MEX parameter based on a characteristic of the object and to control at least one of the X-ray source and the energy identification detector based on the generated optimal MEX parameter.

20 Claims, 3 Drawing Sheets

APPARATUS AND METHOD FOR ACQUIRING OPTIMAL MULTI-ENERGY X-RAY IMAGE

CROSS-REFERENCE TO RELATED APPLICATION

This application claims priority from Korean Patent Application No. 10-2012-0118755, filed on Oct. 25, 2012, in the Korean Intellectual Property Office, the entire disclosure of which is incorporated herein by reference.

BACKGROUND

1. Field

Methods and apparatuses consistent with exemplary embodiments relate to acquiring an optimal multi-energy X-ray (MEX) image that may optimize various variable imaging parameters, and may acquire an image optimized to a characteristic of an object, to improve a quality of a final image.

2. Description of the Related Art

X-rays are widely used in various fields, for example, to obtain medical information of patients.

X-rays are generated while an electron generated in a cathode filament is bumped against an anode target. When the generated X-rays are irradiated to an object, the X-rays are attenuated based on a material and characteristic of the object, and X-rays passing through the object form an image on a detector installed behind an object.

Many X-ray systems display images by using an attenuation characteristic that is detected when the X-rays with a single energy band pass through an object. In the above X-ray systems, when materials forming the object have different attenuation characteristics, an image with a good quality may be obtained. However, when the materials have similar attenuation characteristics, a quality of an image may be degraded.

A MEX system may acquire an X-ray image of at least two energy bands. Since materials typically exhibit different X-ray attenuation characteristics in different energy bands, images can be separated for each material.

A MEX technology is used to increase a contrast between materials using a difference in absorption characteristics of materials of a human body changed based on energy. A related art MEX technology uses two methods: a multiple exposure method and a single exposure method.

However, in a MEX system, a great number of imaging parameters may need to be selected. The imaging parameters may include, for example, a source parameter, such as a tube voltage, a tube current, a filter, and the like, and a detector parameter, such as an energy threshold of a photon counting detector (PCD), and the like.

Additionally, noise, contrast enhancements, and image processing of an original MEX image may cause deterioration in quality of a finally obtained image. Thus, to improve the quality of the final image based on the selected an imaging parameter, it is desirable to select an optimal imaging parameter to obtain a final image of a high quality.

In a related art method of selecting a single imaging parameter, such as in an automated exposure control (AEC) method, an imaging parameter of an X-ray tube, for example a tube voltage, a tube current, an exposure time, and the like may be selected.

A related art dual or multi-energy imaging method is limited to a parameter selection of an X-ray source, for example, a dual tube voltage, a dual exposure, a dual layer, a dual source scheme and the like.

SUMMARY

Exemplary embodiments may address at least the above problems and/or disadvantages and other disadvantages not described above.

According to an aspect of an exemplary embodiment, there is provided an apparatus for acquiring a MEX image, including an X-ray source to generate an X-ray and to irradiate the X-ray, an energy identification detector to acquire a MEX image, the MEX image being generated when the irradiated X-ray penetrates an object to be imaged, and an optimal MEX processor to generate an optimal MEX parameter based on a characteristic of the object, and to control at least one of the X-ray source and the energy identification detector based on the generated optimal MEX parameter.

The characteristic of the object may include at least one of a thickness of the object, a type of a contrast medium injected into the object, a dose of the contrast medium, and a density of the object.

The optimal MEX processor may include an information collector to collect information to generate an optimal MEX parameter, and a parameter selector to select an optimal MEX parameter, using the collected information.

The apparatus may further include an X-ray source controller to control the X-ray source based on a source parameter extracted from the selected optimal MEX parameter.

The source parameter may include at least one of a type of a material of an anode target, a tube voltage, a tube current, and an exposure time.

The apparatus may further include an energy identification detector controller to control the energy identification detector based on a detector parameter extracted from the selected optimal MEX parameter.

The detector parameter may include at least one of a threshold and a threshold offset table.

The optimal MEX processor may include a MEX system simulator to determine a quality of a final image based on collected parameters through system modeling and simulation, and to select the optimal MEX parameter.

The MEX system simulator may define information regarding at least one of the X-ray source, the energy identification detector and a phantom, and may perform modeling.

The MEX system simulator may calculate a spectrum shape changed based on an anode target, a filter and a tube voltage, may calculate a dose obtained by multiplying a tube current and an exposure time, and may perform modeling of the X-ray source.

The MEX system simulator may estimate a detector response through detector threshold scan, and may perform modeling of the energy identification detector.

The MEX system simulator may perform modeling of the phantom based on a tissue-equivalent material having the same X-ray absorption characteristic.

According to an aspect of an exemplary embodiment, there is provided a method of acquiring a MEX image, including generating an optimal MEX parameter based on a characteristic of an object to be captured, and controlling at least one of an X-ray source and an energy identification detector based on the generated optimal MEX parameter.

The optimal MEX parameter may include at least one of a source parameter associated with a control condition of the X-ray source, and a detector parameter associated with a control condition of the energy identification detector.

The source parameter may include at least one of a type of a material of an anode target, a tube voltage, a tube current, and an exposure time.

The detector parameter may include at least one of a threshold and a threshold offset table.

BRIEF DESCRIPTION OF THE DRAWINGS

The above and/or other aspects of exemplary embodiments will become more apparent by describing certain exemplary embodiments, with reference to the accompanying drawings, in which.

DETAILED DESCRIPTION

Figure 1:
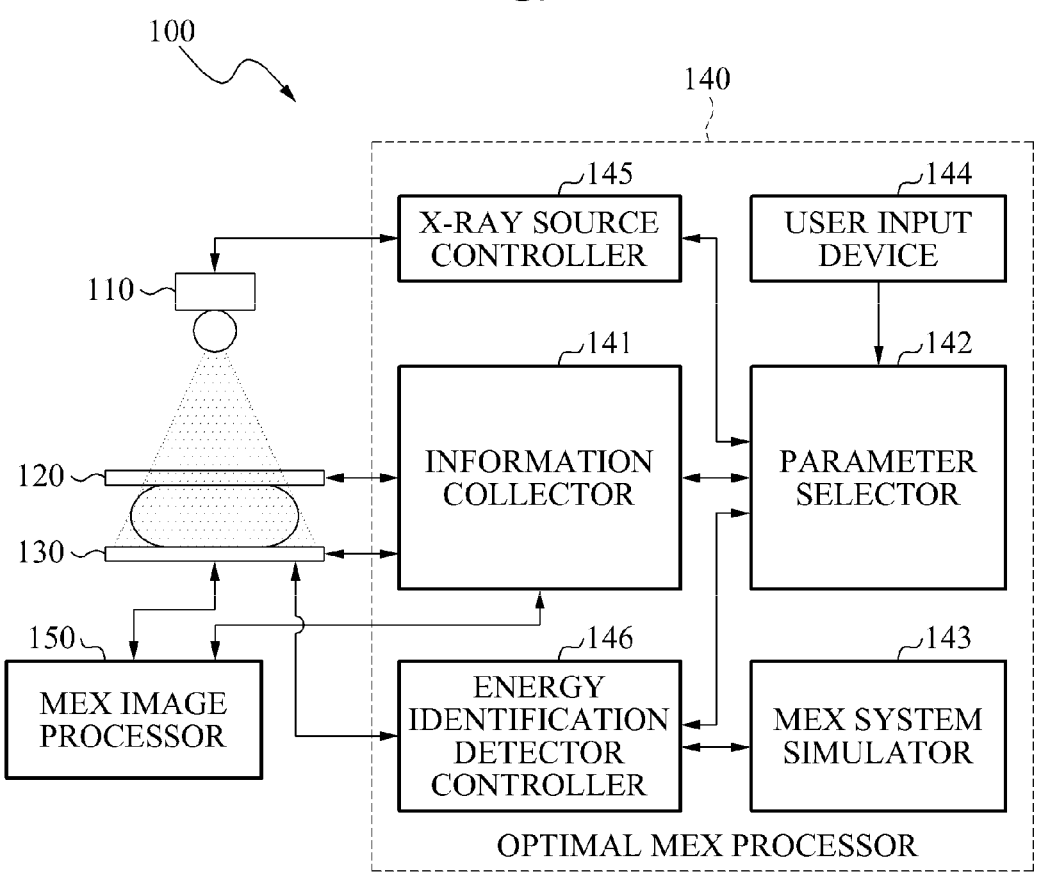
FIG. 1 is a diagram illustrating an apparatus for acquiring a MEX image according to an exemplary embodiment.

Below, certain exemplary embodiments are described in greater detail with reference to the accompanying drawings.

In the following description, like reference numerals are used for the like elements, even in different drawings. The matters defined in the description, such as detailed construction and elements, are provided to assist in a comprehensive understanding of exemplary embodiments. However, exemplary embodiments can be carried out without those specifically defined matters. Also, well-known functions or constructions are not described in detail since that would obscure the description with unnecessary detail.

FIG. 1 is a diagram illustrating an apparatus 100 for acquiring MEX image according to an exemplary embodiment.

Referring to FIG. 1, the apparatus 100 may include an X-ray source 110, a compressor 120, an energy identification detector 130, and a MEX processor 140.

The X-ray source 110 may generate an X-ray, and may irradiate the generated X-ray to an object to be imaged.

The X-ray source 110 may be controlled based on a tube voltage, a tube current, a type of an anode target, a type of a filter, or a thickness of the filter that is selected by an X-ray source controller 145.

The compressor 120 may apply a predetermined pressure to the object, to acquire various images. For convenience of description, a breast is described as an example of the object.

The energy identification detector 130 may acquire a MEX image. The MEX image may be generated when the irradiated X-rays penetrate the breast.

The energy identification detector 130 may acquire images of a plurality of energy bands, by inputting a plurality of energy thresholds or using an energy threshold offset table determined based on the plurality of energy thresholds.

The apparatus 100 may optimize various imaging parameters, and may acquire an image optimized to a characteristic of the breast, to improve a quality of a final image.

The MEX processor 140 may generate an optimal MEX parameter, based on a characteristic of the object, and may control at least one of the X-ray source 110 and the energy identification detector 130, based on the generated optimal MEX parameter.

For example, the characteristic of the object may be a thickness of the object, a type of a contrast medium injected into the object, a dose of the contrast medium, a density of the object, and the like.

The MEX processor 140 may improve a quality of an image acquired by optimizing a plurality of imaging parameters that are associated with the X-ray source 110 or the energy identification detector 130.

The MEX processor 140 may include an information collector 141, a parameter selector 142, a MEX system simulator 143, a user input device 144, the X-ray source controller 145, and an energy identification detector controller 146.

The information collector 141 may collect the information that is generated during a preparation stage and/or during acquiring of the MEX image, to generate an optimal MEX parameter.

An example of the information collector 141 is further described below with reference to FIG. 2.

Figure 2:
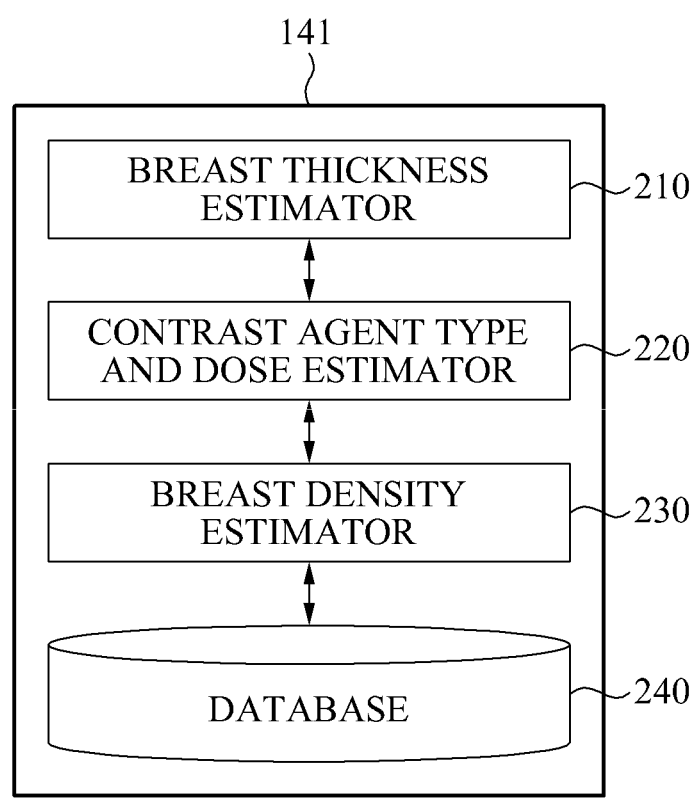
FIG. 2 is a block diagram illustrating an information collector according to an exemplary embodiment.

FIG. 2 is a block diagram illustrating an information collector 141 according to an exemplary embodiment.

Referring to FIG. 2, the information collector 141 may include a breast thickness estimator 210, a contrast agent type and dose estimator 220, a breast density estimator 230, and a database 240.

The breast thickness estimator 210 may check a degree of a pressure applied by the compressor 120 of FIG. 1, and may estimate a thickness of a breast to be imaged based on the degree of a pressure.

The contrast agent type and dose estimator 220 may estimate a type and a dose of a contrast agent, which is determined to be used based on a density of the breast.

The breast density estimator 230 may estimate the density of the breast, by performing a preshot or pre-examination analysis.

Information regarding the density and the thickness of the breast may be used for selection of an optimal imaging parameter.

The information regarding the density and the thickness of the breast may be recorded in the database 240. The breast thickness estimator 210 and/or the breast density estimator 230 may extract previous data obtained by imaging the same patient from the database 240, and may use the extracted previous data.

Referring back to FIG. 1, the parameter selector 142 may select an optimal MEX parameter, based on a breast density, a breast thickness, whether a contrast agent is to be injected, and a dose of the determined contrast agent, based on predicted information.

For example, the parameter selector 142 may acquire breast characteristic information and system model information, and may select an optimal MEX parameter including at least one of an optimal source parameter and an optimal detector parameter, which may maximize a quality of a final image, based on the acquired breast characteristic information and the acquired system model information.

The parameter selector 142 may divide the selected optimal MEX parameter into a source parameter and a detector parameter, may transmit the source parameter to the X-ray source controller 145, and may transmit the detector parameter to the energy identification detector controller 146.

The source parameter may include a parameter used to determine a shape of a spectrum and an energy range of an X-ray. The source parameter may include, for example, a type of a material of an anode target, a tube voltage, a tube current, and/or an exposure time. The tube voltage may be expressed in kilovolt peak (kVp), a tube current may be expressed in milliamps, and an exposure time may be expressed in seconds. The tube current may be used to determine an X-ray filter, a dose, and a quantum noise.

The detector parameter may include an energy threshold, and/or an energy threshold offset table. The threshold may be used to define an energy range of each multi-energy image, and may be expressed in millivolts (mV) or in energy units. The energy threshold offset table may be used to calibrate a threshold of a PCD to obtain an accurate energy image matched to an input threshold.

The energy threshold offset table may be changed based on an input threshold, may be determined in advance, and/or may be stored in a memory.

The detector exposure time information may also be transmitted. The detector exposure time information may be used for an operation of a detector based on a source exposure time.

The MEX system simulator 143 may determine a quality of a final image based on collected parameters by performing system modeling and simulation, and may select the optimal MEX parameter to obtain a final image of an expect high quality.

To select an optimal parameter, a desired quality of a final image may be determined by performing imaging with respect to all possible parameter combinations. However, since problems, for example, constraints by imaging times, a reduction in lifetime of equipment, and the like may occur due to performing the imaging based on all of the combinations, a quality of a final image may be determined using the MEX system simulator 143.

For system modeling and simulation, the MEX system simulator 143 may define information regarding an X-ray source, an energy identification detector, and a phantom that are included in a multi-energy system, and may perform modeling to determine which parameter or parameters would yield the image of a desired quality which conforms, for example, to a set of criteria or quality parameters determined automatically or provided by a user.

For example, the MEX system simulator 143 may calculate a spectrum shape and a dose obtained by multiplying a tube current and an exposure time, and may perform modeling of the X-ray source. The spectrum shape may be changed based on an anode target, a filter and/or a tube voltage.

In another example, the MEX system simulator 143 may estimate a detector response by performing a detector threshold scan, and perform modeling of the energy identification detector.

The detector response may be the information that reflects a non-ideal energy characteristic of a PCD, for example, charge sharing, energy dispersion, fluorescence x-ray escape/reabsorption, a pulse pileup, and the like. The detector response may be inverse-estimated from a difference between an input spectrum and an output spectrum obtained through scanning of a threshold of the PCD, using an X-ray source with known parameters.

The MEX system simulator 143 may perform modeling of the phantom based on a tissue-equivalent material having the same X-ray absorption characteristic. The tissue-equivalent material may correspond to, for example, adipose tissues, glandular tissues, fibrous tissues, a cancerous mass, microcalcification, and the like.

A simulation may be performed on few or all of the possible parameter combinations based on information collected through the above modeling processes, and an expected quality of a final image may be determined.

A final image of a MEX system may be defined to be a high-contrast image. For example, the final image may be obtained by generating a virtual low energy image from a plurality of MEX images, generating a tissue enhanced image using a difference between the virtual low energy image and a high energy image, and obtaining a combination of the tissue enhanced image and a full energy image.

To select an optimal MEX parameter, a signal difference to noise ratio (SDNR) of a foreground region, that is, a cancerous region, and a background region in a final image may be used to set the desired quality parameters.

For example, in a technology associated with a mammography, as a result of selecting an optimal MEX parameter, a high tube voltage equal to or higher than 40 kVp may be used, a K-edge filter of Ag, Rh, and the like may be used, and one of the energy thresholds may be determined to be energy corresponding to a K-edge.

The user input device 144 may receive at least one of a source parameter and a detector parameter that may be input by a user.

The X-ray source controller 145 may control an X-ray source using the source parameter. The energy identification detector controller 146 may control an energy identification detector using the detector parameter.

The apparatus 100 may further include a MEX image processor 150 which may process a MEX image obtained using an optimal MEX parameter, and may generate, save and display a final image.

Figure 3:
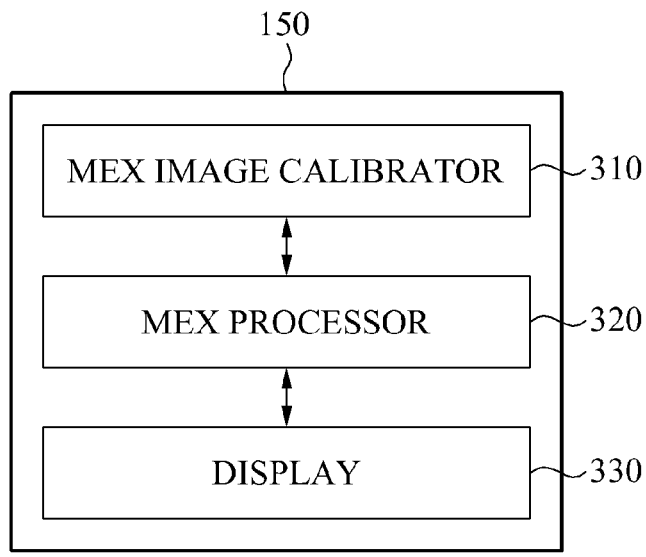
FIG. 3 is a block diagram illustrating a MEX image processor according to an exemplary embodiment.

FIG. 3 is a block diagram illustrating a MEX image processor 145 according to an exemplary embodiment.

The MEX image processor 145 may include a MEX image calibrator 310, a MEX processor 320, and a display 330.

The MEX image calibrator 310 may perform MEX calibration to reduce an artifact and noise of an acquired image. The MEX calibration may include, for example, gain correction, artifact correction, dead pixel correction, and the like.

The MEX processor 320 may process a plurality of MEX images to obtain the images that are easily used for diagnosis.

For example, to acquire a single high-contrast image from a plurality of MEX images, the MEX processor 320 may generate a virtual low energy image from the plurality of MEX images, generate a tissue enhanced image by subtracting the virtual low energy image from a high energy image, and obtain a combination of the tissue enhanced image and a full energy image.

Thus, it is possible to improve a quality of a final image, by optimizing various variable imaging parameters, and by acquiring an image optimized to a characteristic of an object, in an MEX system using a PCD.

Figure 4:
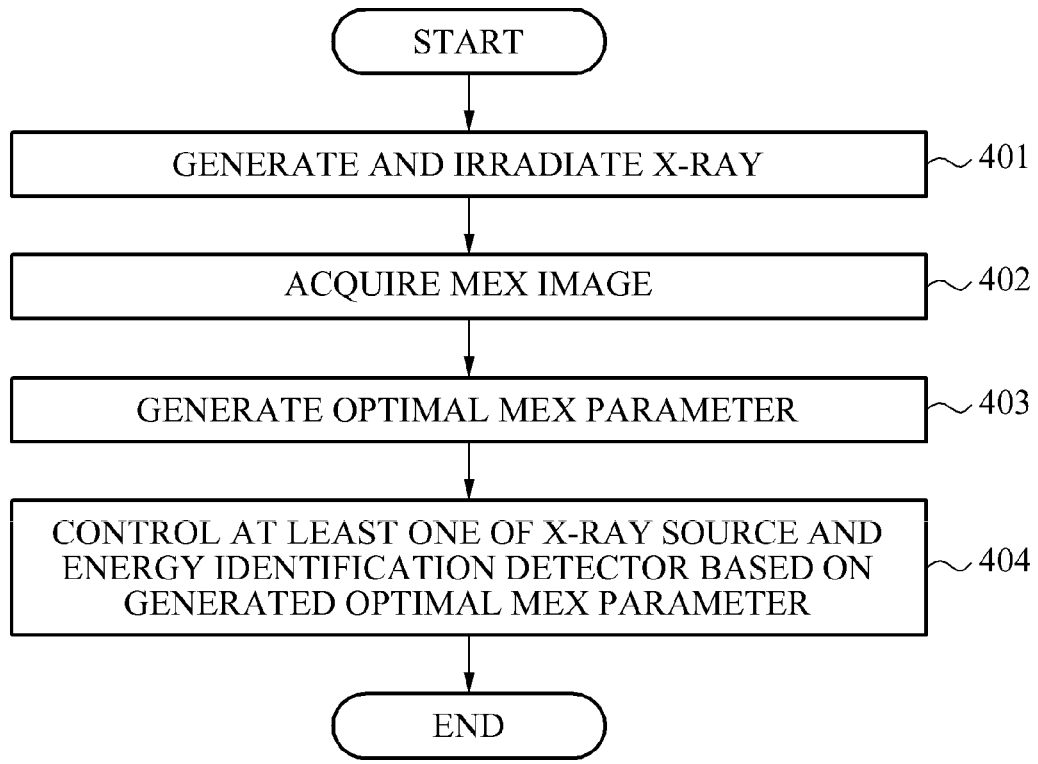
FIG. 4 is a flowchart illustrating a method of acquiring a MEX image according to an exemplary embodiment.

FIG. 4 is a flowchart illustrating a method of acquiring a MEX image according to an exemplary embodiment.

Referring to FIG. 4, in operation 401, X-rays may be generated and irradiated. In operation 402, a MEX image may be acquired. The MEX image may be generated when the X-rays penetrate an object to be imaged.

In operation 403, an optimal MEX parameter may be generated.

Specifically, in the method of FIG. 4, information to generate the optimal MEX parameter may be collected, and the optimal MEX parameter may be selected using the collected information.

For example, the optimal MEX parameter may be generated based on a characteristic of the object.

For example, the characteristic of the object may be interpreted to be a thickness of the object, a type of a contrast medium injected into the object, a dose of the contrast medium, a density of the object, and the like.

In operation 404, at least one of an X-ray source and an energy identification detector may be controlled based on the generated optimal MEX parameter.

The methods of acquiring a MEX image according to the above-described exemplary embodiments may be recorded in computer-readable media via program instructions to implement various operations embodied by a computer. The media may also include, alone or in combination with the program instructions, data files, data structures, and the like. Examples of computer-readable media include magnetic media such as hard disks, floppy disks, and magnetic tape; optical media such as CD ROM disks and DVDs; magneto-optical media such as optical disks; and hardware devices that are specially configured to store and perform program instructions, such as read-only memory (ROM), random access memory (RAM), flash memory, and the like. Examples of program instructions include machine code, such as produced by a compiler, and files containing higher level code that may be executed by the computer using an interpreter. The described hardware devices may be configured to act as one or more software modules in order to perform the operations of the above-described exemplary embodiments, or vice versa.

Although a few exemplary embodiments have been shown and described, it would be appreciated by those skilled in the art that various changes in form and detail may be made in these exemplary embodiments without departing from the spirit and scope of the disclosure, the scope of which is defined by the claims and their equivalents.

What is claimed is:

1. An apparatus for acquiring an X-ray image, the apparatus comprising:
    an X-ray source which generates X-rays and irradiates the X-rays onto an object;
    a detector which acquires the X-ray image being generated when the X-rays penetrate the object; and
    a processor which generates a source optimal parameter and a detector optimal parameter based on a characteristic of the object, and controls the X-ray source and the detector based on the generated source optimal parameter and the generated detector optimal parameter, respectively,
    wherein the processor generates the source optimal parameter and the detector optimal parameter by:
    simulating a plurality of parameters related to the X-ray source and the detector, and
    selecting the source optimal parameter and the detector optimal parameter from the plurality of parameters.

2. The apparatus of claim 1, wherein the characteristic of the object comprises at least one of a thickness of the object, a type of a contrast medium to be injected into the object, a dose of the contrast medium, and a density of the object.

3. The apparatus of claim 1, wherein the processor comprises:
    an information collector which collects information for generating the source optimal parameter and the detector optimal parameter; and
    a parameter selector which selects the source optimal parameter and the detector optimal parameter, based on the collected information.

4. The apparatus of claim 1, wherein the processor comprises:
    an X-ray source controller which controls the X-ray source based on the selected source optimal parameter.

5. The apparatus of claim 1, wherein the source optimal parameter comprises at least one of a type of a material of an anode target, a tube voltage, a tube current, and an exposure time.

6. The apparatus of claim 1, wherein the processor comprises:
    a detector controller which controls the detector based on the selected detector optimal parameter.

7. The apparatus of claim 1, wherein the detector optimal parameter comprises at least one of an energy threshold and an energy threshold offset table.

8. An apparatus for acquiring an X-ray image, the apparatus comprising:
    an X-ray source which generates X-rays and irradiates the X-rays onto an object;
    a detector which acquires the X-ray image being generated when the X-rays penetrate the object; and
    a processor which generates an optimal parameter based on a characteristic of the object, and controls at least one of the X-ray source and the detector based on the generated optimal parameter,
    wherein the processor comprises:
    a system simulator which determines a quality of a final image based on a plurality of parameters by performing modeling and simulation and selects the optimal parameter, from the plurality of parameters.

9. The apparatus of claim 8, wherein the system simulator defines information regarding at least one of the X-ray source, the detector and a phantom, and performs modeling.

10. The apparatus of claim 9, wherein the system simulator calculates a spectrum shape changed based on an anode target, a filter and a tube voltage, calculates a dose obtained by multiplying a tube current and an exposure time, and performs modeling of the X-ray source.

11. The apparatus of claim 9, wherein the system simulator estimates a detector response by performing a detector threshold scan, and performs modeling of the detector.

12. The apparatus of claim 9, wherein the system simulator performs modeling of the phantom based on a tissue-equivalent material having the same X-ray absorption characteristic as that of a tissue to be imaged.

13. A method of acquiring an X-ray image, the method comprising:
    generating a source optimal parameter and a detector optimal parameter, based on a characteristic of an object to be imaged; and
    controlling an X-ray source and a detector based on the generated source optimal parameter and the generated detector optimal parameter, respectively,
    wherein the generating the source optimal parameter and the detector optimal parameter comprises:
    simulating a plurality of parameters related to the X-ray source and the detector, and
    selecting the source optimal parameter and the detector optimal parameter from the plurality of parameters.

14. The method of claim 13, wherein the source optimal parameter is associated with a control condition of the X-ray source, and
    the detector optimal parameter is associated with a control condition of the detector.

15. The method of claim 13, wherein the source optimal parameter comprises at least one of a type of a material of an anode target, a tube voltage, a tube current, and an exposure time.

16. The method of claim 13, wherein the detector optimal parameter comprises at least one of an energy threshold and an energy threshold offset table.

17. A non-transitory computer-readable recording medium storing a program which, when executed by a computer, causes the computer to execute the method of claim 13.

18. An X-ray imaging apparatus comprising:
an X-ray source which generates X-rays and irradiates the X-rays onto an object;
a detector which acquires an image being generated when the X-rays penetrate the object; and
a processor which controls at least one of the X-ray source and the detector based on an optimal parameter which is generated by:
determining an object parameter peculiar to the object,
modeling the X-ray source based on the object parameter to obtain source parameters,
modeling the detector based on the source parameters, and
selecting an optimal source parameter and an optimal detector parameter.

19. The apparatus of claim 18, wherein the optimal parameter is further generated by:
iteratively simulating the X-ray source and the detector based on a phantom which possesses the same X-ray absorption characteristics as that of a tissue to be imaged in the object,
determining whether an image generated as a result of a simulation is within a range of set quality parameters, and
selecting the optimal source parameter and the optimal detector parameter, from simulation results, when the image is determined to be within the range of the set quality parameters.

20. The apparatus of claim 18, wherein the object parameter comprises at least one of a thickness of the object, a type of a contrast medium to be injected into the object, a dose of the contrast medium, and a density of the object, and is determined during a pre-examination proceeding.

* * * * *